(12) United States Patent
De Moyer

(10) Patent No.: US 7,731,497 B2
(45) Date of Patent: Jun. 8, 2010

(54) METHOD FOR MANUFACTURING A DENTAL PROSTHESIS AND AN APPLIANCE FOR IMPLANTATION THEREOF

(76) Inventor: Philippe Albert Paul Ghislain De Moyer, Den Draaier, 22, Beersel (BE) 1650

( * ) Notice: Subject to any disclaimer, the term of this patent is extended or adjusted under 35 U.S.C. 154(b) by 277 days.

(21) Appl. No.: 11/815,115

(22) PCT Filed: Feb. 1, 2006

(86) PCT No.: PCT/EP2006/050584

§ 371 (c)(1),
(2), (4) Date: Jul. 31, 2007

(87) PCT Pub. No.: WO2006/082198

PCT Pub. Date: Aug. 10, 2006

(65) Prior Publication Data

US 2008/0153060 A1  Jun. 26, 2008

(30) Foreign Application Priority Data

Feb. 3, 2005 (BE) .................................. 2005/0061

(51) Int. Cl.
*A61C 19/04* (2006.01)
(52) U.S. Cl. ........................................................ 433/72
(58) Field of Classification Search ............. 433/75–76, 433/172–174, 213–215, 24, 72; 606/96–97

See application file for complete search history.

(56) References Cited

U.S. PATENT DOCUMENTS

| 5,967,777 | A | 10/1999 | Klein et al. |
| 6,514,258 | B1 | 2/2003 | Brown et al. |

FOREIGN PATENT DOCUMENTS

| EP | 1 532 939 A1 | 5/2005 |
| FR | 2 808 669 A1 | 11/2001 |
| WO | WO 03/073954 A1 | 9/2003 |
| WO | WO 2004/017860 A1 | 3/2004 |
| WO | WO 2004/075771 A1 | 9/2004 |
| WO | 2008/006802 A1 | 1/2008 |
| WO | 2009/027316 A1 | 3/2009 |

*Primary Examiner*—Cris L Rodriguez
*Assistant Examiner*—Matthew M Nelson
(74) *Attorney, Agent, or Firm*—Sughrue Mion, PLLC

(57) ABSTRACT

A method of manufacturing a dental prosthesis to be implanted in a jaw of a patient, including the production of a radiological guide whose image, when the guide is placed in position on the jaw of the patient, can be processed for introducing virtual implants and guide cylinders in a surgically appropriate position; drilling holes into the guide on the basis of information obtained from the processing and placing real guide cylinders into the holes in order to form a surgical guide; placing the surgical guide on a pattern of the patient's jaw and drilling holes into the pattern through the guide cylinders; placing implant analogues into the holes drilled into the pattern; and producing the dental prosthesis on the pattern. Also, an appliance for carrying out the manufacturing method.

9 Claims, 6 Drawing Sheets

METHOD FOR MANUFACTURING A DENTAL PROSTHESIS AND AN APPLIANCE FOR IMPLANTATION THEREOF

BACKGROUND OF THE INVENTION

The present invention relates to a method of manufacturing a dental prosthesis to be implanted in a jaw of a patient and an appliance used for such an implantation.

Implants are at the moment positioned in four ways:

1. Freehand with a wide cut in the gum and detachment of the latter. Fitting takes place in an archaic manner without any reference or guiding mark with respect to the future prosthesis. Although this technique is the worst and gives results that are often aesthetically, functionally and hygienically disastrous, it is the most widely used. It is also the one that causes the most accidents (rupture of the mandibular nerve, piercing of the sinus, rupture of the cortices, etc).

2. Freehand with a wide cut in the gum and a detachment of the latter, the positioning takes place in a more or less precise manner since the dental laboratory has produced a surgical guide that more or less prefigures the future prosthesis. This technique is the second most widely used but the drawback is that the surgical guide is often unusable because of the cutting of the gum, which prevents the fitting thereof. With this technique there are also often poor results at an aesthetic, functional or hygienic level and accidents as aforementioned are numerous.

3. With the hand guided by drilling guides produced from a computerised plan. This technique makes it possible to place drilling cylinders in these guides at precise points according to the bone or according to the bone and the future prosthesis. Two distinct technologies apply this technique:

Guides are produced from steriolithographic models, that is to say on the basis of images issuing from dental scanning. Artefacts often interfere with the production of these guides not always making it possible to use them through lack of precision.

Guides are produced from an impression and a radiological guide that is produced on the basis of this impression in silicone (rather than on the basis of an image issuing from dental scanning). This radiological guide is then converted into a surgical guide by the insertion of guide cylinders for the drilling and the positioning of implants in the jaw.

These techniques make it possible to reduce damage to the patient and in particular the last technique improves the prosthetic result.

4. Freehand guided by a navigation system (GPS). This technique makes it possible to place an implant more or less precisely. However, it does not prevent all damage to the patient since the drilling is still manual and skidding remains possible. In addition it does not take account of the future prosthesis. This technique is expensive and is the least used.

All these techniques together have the drawback of having to produce the final prosthesis after taking an impression of the jaw where the implants were placed previously, which is carried out several weeks after the positioning of the implants, which is complex and requires many post-operative interventions, which are difficult for the patient.

SUMMARY OF THE INVENTION

The aim of the present invention is to develop a method of manufacturing a dental prosthesis to be implanted in the jaw of the patient that overcomes the aforementioned drawbacks and that makes it possible to simplify the positioning of these prostheses, whilst obtaining increased precision and reliability.

To resolve these problems there has been provided according to the invention a method of manufacturing a dental prosthesis to be implanted in the jaw of a patient, comprising the production, from an impression of the jaw of the patient, a radiological guide, provided with at least one artificial radiological tooth and radiological references, computer processing of a radiological image in two dimensions representing the above-mentioned radiological guide in position on the jaw, so as to form, from this two-dimensional image, a three-dimensional image, in the images in two and three dimensions, an insertion, per tooth, of a virtual implant in a surgically appropriate position in the image of the jaw and a virtual guide cylinder oriented coaxially with the virtual implant in the image of the radiological guide, producing, from the data collected and calculated by the computer during the said steps of image processing and insertion of the virtual implant and virtual guide cylinder, a surgical guide by a first drilling, in each artificial tooth supported by the radiological guide, of a first hole appropriate for receiving a guide cylinder disposed and oriented like the corresponding virtual guide cylinder of the images in two and three dimensions, and by placing in each first drilled hole such a guide cylinder provided with at least one external reference, placing the surgical guide on a pattern obtained from the said impression, a second drilling, guided through each guide cylinder, of a second hole through this pattern, placing, in each second hole, an implant analogue by sliding into the guide cylinder an analogue holder that carries the above-mentioned implant analogue, as far as a depth corresponding to that of the virtual implant on the images in two and three dimensions, and by matching, by rotation, at least a second external reference provided on the analogue holder with the said first external reference of the guide cylinder, the said implant analogue having dimensions corresponding to those of the virtual implant selected for insertion in the images in two and three dimensions which corresponds to a real implant to be placed in the jaw of the patient, and the said implant analogue holder being identical to an implant holder selected for the implantation of the said real implant to be placed, fixing the implant analogue in its hole, as placed, after removing each analogue holder and the surgical guide, making a definitive dental prosthesis adapted to the pattern provided with the implant analogue or analogues, this prosthesis thus being able to be fixed to the selected implants after they are implanted in the jaw in a manner that is guided by the surgical guide and identical to that used for the placing of the implant analogues in the pattern.

This method offers the great advantage of determining by image the position of each of the implants to be implanted in an ideal position in the jaw, according to the situation of the mandibular nerves, sinuses, etc. Through the appropriate guidance of the invention, it is possible in a reproducible manner to introduce into a pattern and subsequently in the same way into the jaw an implant analogue and respectively a similar implant. This introduction is always carried out so that the implant and the implant analogue are fixed in their support brackets (pattern or jaw) with the position determined on the images in two and three dimensions, this is to say with the same axial orientation and at the same depth. In addition, by an appropriate marking, it is possible, according to the invention, for the head of the implant and that of the implant analogue, which generally have the shape of a prism with a triangular or polygonal cross section and on which the prosthesis is then placed, to be situated in rotation in a precise position, which will be the same in both cases. This offers the exceptional advantage of being able to produce the unitary or multiple definitive prosthesis on a pattern, even before the placing of the implants, and to place this prosthesis on the implants, on the day when these are placed in position.

According to a particular embodiment of the invention, the method also comprises

- fashioning, from the said impression, at least one pattern, on which there is produced a mounting provided with false teeth adaptable in the mouth,
- producing a mounting key,
- after removal of the said false teeth, pouring, in the key mounted on the pattern, a material visible in radiological imaging, and hardening it in the form of an arc,
- dividing the hardened arc into individual artificial radiological teeth which, replaced in the key, are fixed on the pattern, and
- after removing the key, producing the said radiological guide by depositing a self-hardening resin on the artificial radiological teeth fixed to the pattern.

This method makes it possible to make an image of a radiological guide provided with individual artificial teeth, very close to what will be necessary for the prosthesis. Advantageously, these artificial teeth consist of a material visible in radiological imaging, which, preferably, is a mixture of resin normally used for fashioning artificial teeth and barium sulphate. This is introduced into the mixture for example in a proportion of about 30% by volume.

Other particularities of the method according to the invention are indicated in the accompanying claims.

Another aim of the present invention is to present an appliance intended for a dental implantation in a jaw of a patient, in particular an appliance capable of implementing the method indicated above.

For this purpose there has been provided, according to the invention, an appliance intended for a dental prosthesis implantation in a jaw of a patient, comprising

- at least one pattern produced from an impression of the jaw of the patient,
- a radiological guide, also produced from this impression, and provided with at least one artificial radiological tooth and radiological references,
- a computer,
- an image processing program for controlling the computer so as to make up, from a two-dimensional radiological image of the above-mentioned radiological guide in position on the jaw of the patient, a three-dimensional image and to insert in these images in two and three dimensions, per tooth, a virtual implant selected in a surgically appropriate position in the image of the jaw and a virtual selected guide cylinder orientated coaxially with the virtual implant in the image of the radiological guide,
- a positioning and drilling tool in which the radiological guide is positioned by means of its radiological references, this tool being capable, on the basis of data collected and calculated by the computer in relation to the images in two and three dimensions, to drill in each of the teeth of the radiological guide a first hole in order to receive a guide cylinder disposed and oriented like the virtual guide cylinder on the images in two and three dimensions,
- a guide cylinder to be housed in each of the first holes drilled in the radiological guide that thus becomes a surgical guide, each guide cylinder being provided with at least one first external reference,
- a least a first drill bit which, when the surgical guide is in position on the pattern, can be guided through each guide cylinder and is capable of drilling there, in the pattern, a second hole according to the orientation of the corresponding guide cylinder,
- an implant analogue corresponding to each virtual implant selected to be housed in each second drilled hole in the pattern, using an analogue holder to be slid axially through the corresponding guide cylinder, each analogue holder comprising stop means that stop the sliding of the analogue holder with respect to the guide cylinder when the analogue is in a position corresponding to the surgically appropriate position of the images in two and three dimensions, and at least one second external reference to be matched, by rotation, with the said at least one first external reference of the guide cylinder,
- a dental prosthesis adaptable to the pattern provided with the above-mentioned implant analogue or analogues,
- at least a second drill bit which, when the surgical guide is in position on the jaw of the patient, can be guided through each guide cylinder and is capable of drilling there third holes in the jaw according to the orientation of the guide cylinder, the said at least one second drill bit comprising stop means which, against the guide cylinder, stop a penetration of the drill bit at a depth that corresponds to that of the said surgically appropriate position of the virtual implant on the images in two and three dimensions, and
- an implant corresponding to each virtual implant selected to be housed in each third hole in the jaw by means of an implant holder to be slid axially through the corresponding guide cylinder, each implant and its implant carrier having dimensions and shapes identical to the implant analogue and to its analogue holder used in the pattern, each implant holder thus comprising stop means that stop the sliding of the implant holder in the guide cylinder when the implant is in the above-mentioned surgically appropriate position, and at least a third external reference to be matched, by rotation, with the said at least one first external reference of the guide cylinder, the implants thus fixed in the jaw being in position so as to receive the dental prosthesis previously implemented on the pattern.

Dental prosthesis means according to the invention any appliance intended to be placed on a dental implant, and in particular a crown, a joining piece, a bar, a bridge, etc.

According to an improved embodiment of the invention each guide cylinder on the one hand and each analogue holder or each implant holder to be slid inside this guide cylinder on the other hand has mutual abutment means that stop a rotation movement of the analogue holder or implant holder with respect to the guide cylinder in a predetermined position, these stop means serving as aforementioned external first and second or respectively third references. Advantageously, each guide cylinder has an axial cavity having an inside diameter, each analogue holder or implant holder or each second drill bit comprising a cylindrical part having an outside diameter allowing guided sliding of this part in the cavity of the guide cylinder and a flange having a diameter greater than the said inside diameter, which serves as the aforementioned stop means.

Other details and particularities of the invention will emerge from the description given below, by way of non-limitative example and with reference to the accompanying drawings, of a method of producing a dental prosthesis according to the invention.

DETAILED DESCRIPTION OF THE INVENTION

In the various drawings, the identical or similar elements bear the same references.

Production of a Radiological Guide

Figure 1:
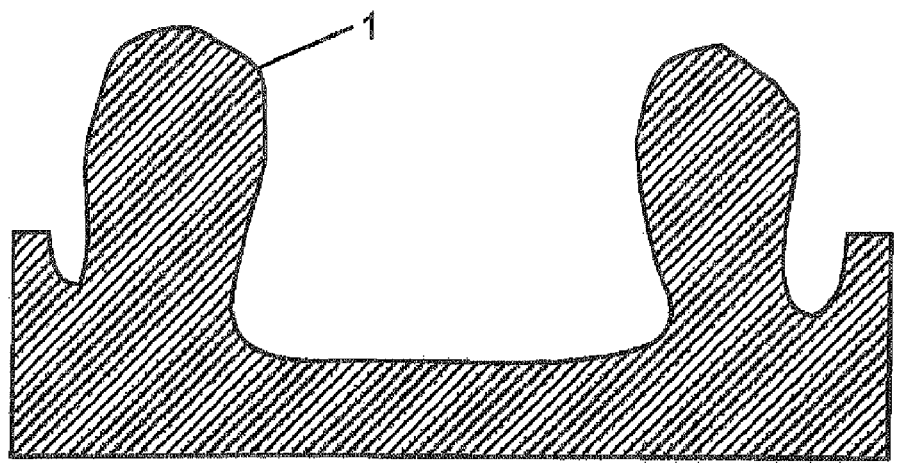
FIGS. 1 to 8 depict, in a view in a cross section, the steps of fabricating a surgical guide according to the invention.

First of all a precise and non-compressive impression of the jaw of the patient is produced in silicone with moderate or low viscosity in order to obtain a three-dimensional mould of the gum and teeth. The same procedure is followed to obtain an impression of the antagonist of the jaw to be treated and thus a mould of this antagonist. From these impressions patterns made from hard plaster are cast, preferably three times for the pattern 1 of the jaw to be treated (see FIG. 1) and once for the antagonist jaw.

Figure 2:
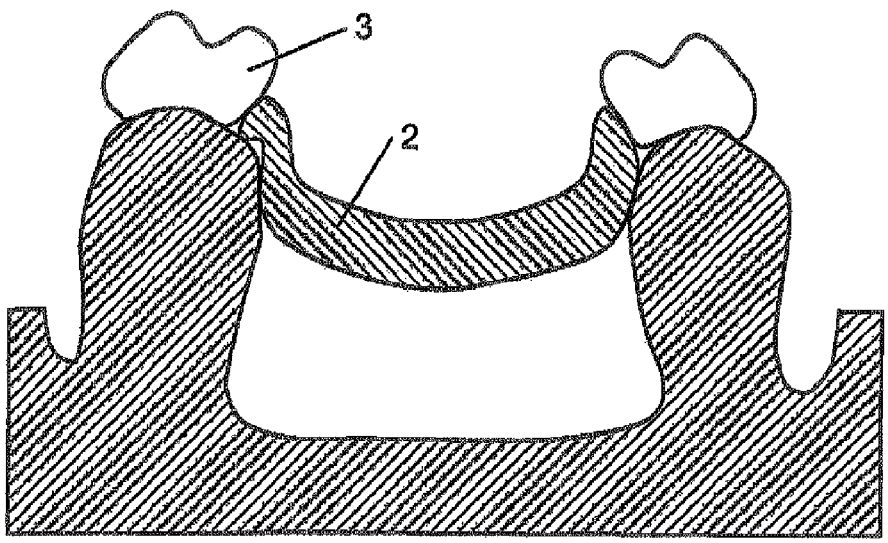
Figure 3:
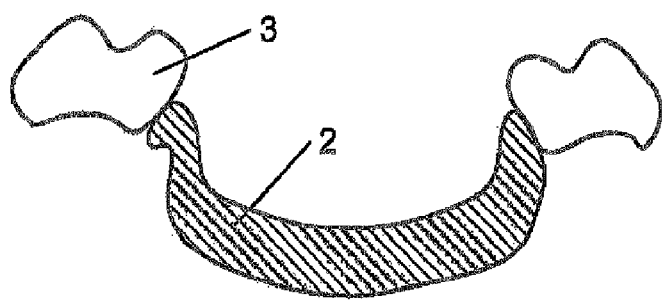
Figure 4:
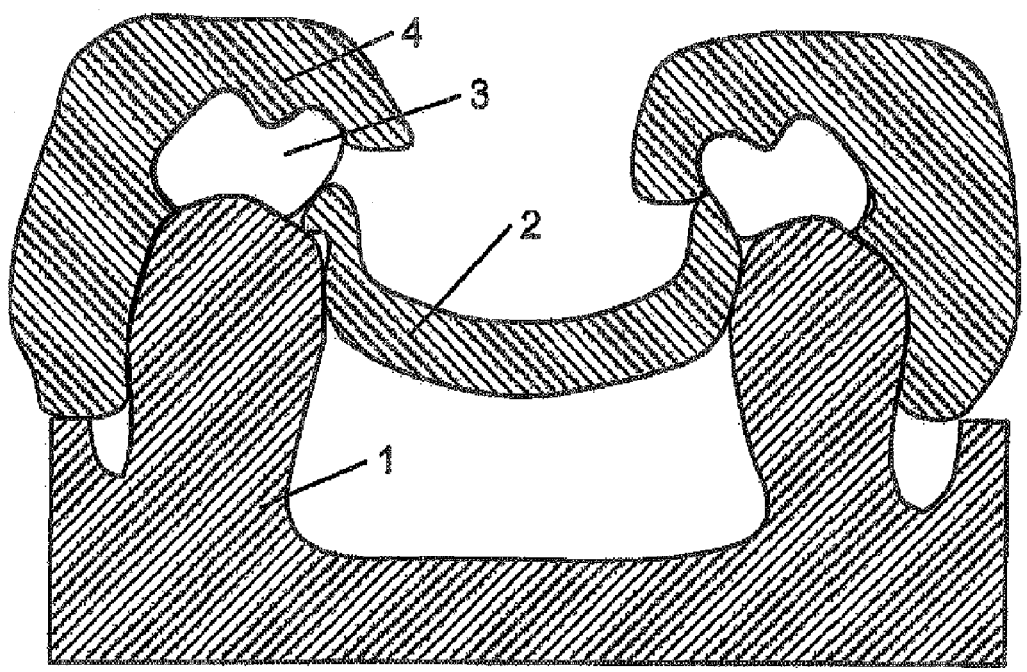
Figure 5:
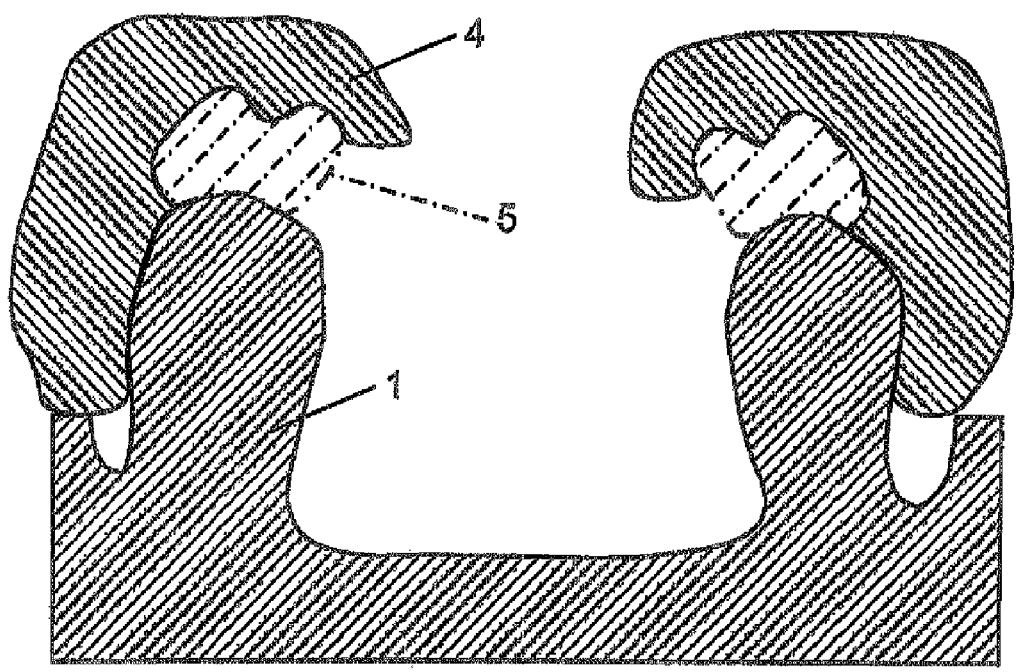

As is clear from FIG. 2, there is then produced on the pattern 1 a precise mounting ("wax-up") by means of a mounting base 2 made from wax or resin and selected false teeth 3, which can be found on the market, for example under the trade name Physiodens. This mounting must prefigure with precision the prosthetic result and must therefore be tried in the mouth by the patient and if appropriate adapted (see FIG. 3).

Figure 6:
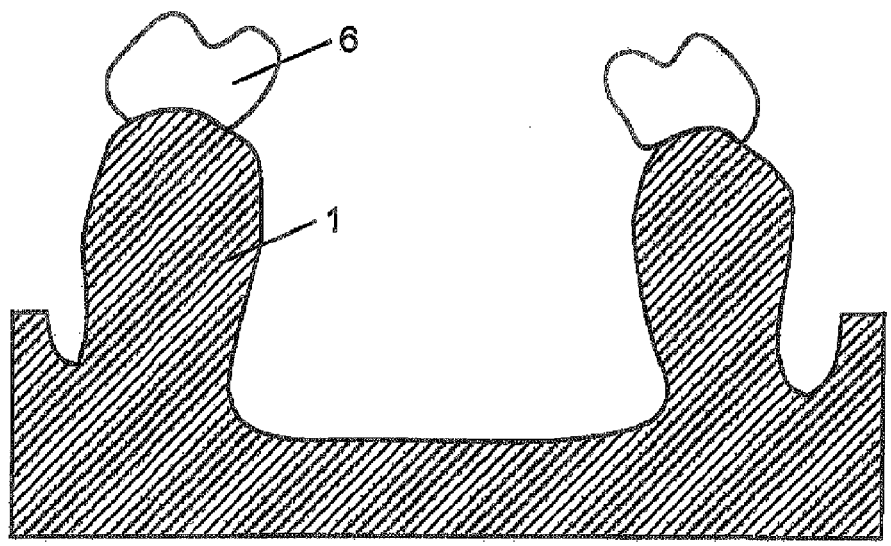

After having removed the key 4 from the pattern 1, the hardened arc 5 is removed and divided into individual teeth 5-6, which are reworked in order to obtain the most natural shape possible. The individual teeth 6 are then replaced in the key 4 ensuring that a space of approximately 0.5 mm remains, without any points of contact between teeth. The key 4 provided with its teeth is replaced on the pattern 1 and a self-polymerising resin is poured on the palatal or lingual side according to circumstances. After hardening of the resin, the key 4 can be removed, the artificial teeth 6 being fixed to the pattern 1 as shown in FIG. 6.

After having removed the key 4 from the pattern 1, the hardened arc 5 is removed and divided into individual teeth 5, which are reworked in order to obtain the most natural shape possible. The individual teeth 6 are then replaced in the key 4 ensuring that a space of approximately 0.5 mm remains, without any points of contact between teeth. The key 4 provided with its teeth is replaced on the pattern 1 and a self-polymerising resin is poured on the palatal or lingual side according to circumstances. After hardening of the resin, the key 4 can be removed, the artificial teeth 6 being fixed to the pattern 1 as shown in FIG. 6.

Figure 7:
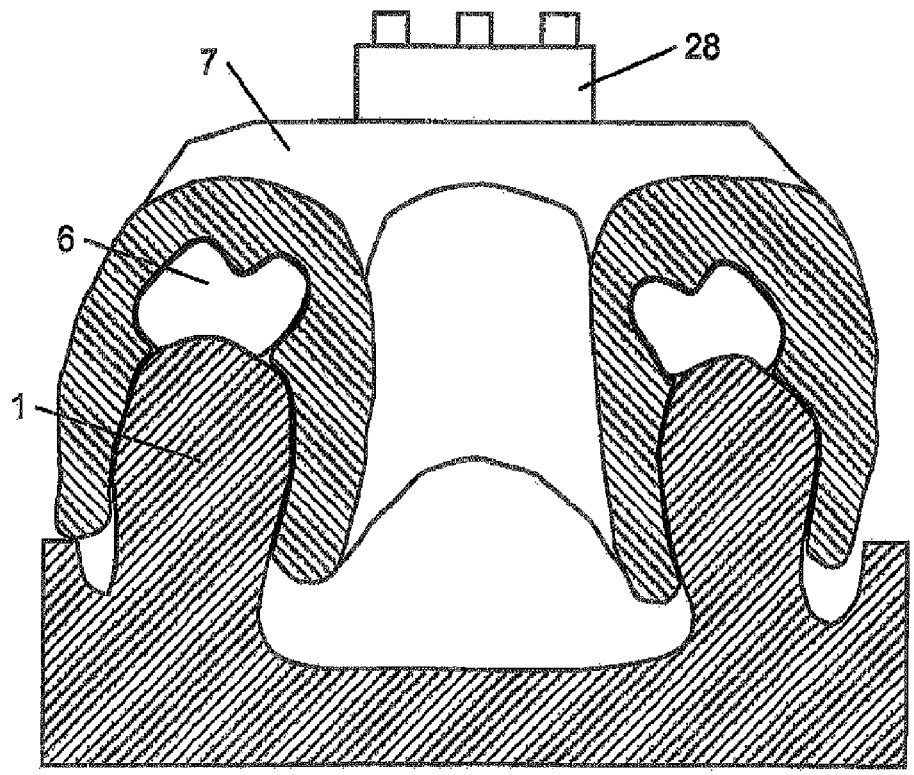

Self-polymerising resin can then be deposited for example on and around the teeth 6 so as to form a guide called the radiological guide 7 (see FIG. 7).

This radiological guide is terminated by stripping it from the pattern 1, eliminating the undercuts at the lowest surface of the guide, and applying on top radiological references that allow spatial positioning of the radiological guide inside the imaging appliance and referencing on the image obtained. Such a reference can consist for example of a Lego block 28 (see FIG. 7) and/or gutta-percha spikes inserted in the guide at appropriate points.

The radiological guide can then be tried once again in the mouth of the patient.

Formation of a Three-Dimensional Image

A two-dimensional image of the radiological guide in position on the jaw of the patient is taken in an appropriate appliance, for example by scanning in a scanner. In a normal manner the data issued from the scanner can for example by recorded on a disc, for example a CD, in DICOM mode.

In a computer these data are processed in order to convert the two-dimensional image into a three-dimensional image. For this the computer is controlled by a suitable program, available on the market, for example the program MED3D distributed by Distridenta Sprl. In these two- and three-dimensional images there naturally appears a jaw, its mandibular nerve, if it is a case of the lower jaw, or a sinus if it is the upper jaw. The radiological guide in a fairly uncontrasted form, as well as the radiological references, can also be seen in these images. The artificial teeth, by virtue of their special composition, stand out clearly and precisely through a bright white colour compared with the rest of the image with a duller colour.

The program makes it possible to select, for each tooth to be implanted, an implant of appropriate type and dimensions (length, diameter) among the implants available on the market and recorded on the data of the computer. It is then possible to introduce this implant in the form of a virtual image into the two- and three-dimensional images of the jaw in a surgically appropriate position. The implants are in fact placed in a virtual manner according in particular to the position of the separate adjoining teeth, the occlusion, the nerve, the sinus and the bone. It is also checked that the quantity of bone is sufficient to obtain osteointegration (1.5 mm) around the implant.

The program also makes it possible to place, in a virtual manner, in the images of the radiological guide, guide cylinders of appropriate height and diameter for the precise case, these parameters being to be determined according to the top of the implant. The virtual guide cylinders are placed coaxially with the virtual implants.

The computer records the coordinates for adjustment of the virtual implants and virtual guide cylinders in the two- and three-dimensional images in an electronically transmissible form.

Production of a Surgical Guide

Figure 8:
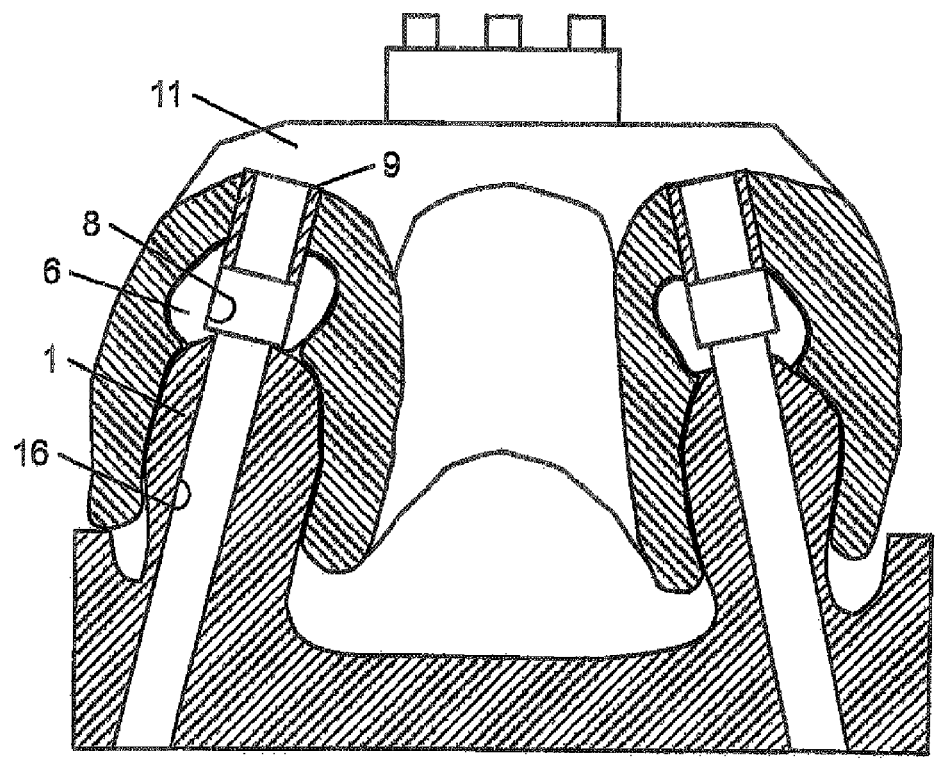

The aforementioned data of the two- and three-dimensional images are transmitted to a suitable positioning and drilling tool, capable of translating and using these data. It is possible to make use for example of an appliance available on the market under the trade name MED3D distributed by Distridenta Sprl. The radiological guide 7 is then placed, for example with plaster, in the positioning tool according to the calculations of the computer. After this positioning in a correct unique position corresponding to each patient, the positioning tool is capable of drilling holes 8 in each of the artificial teeth 6 of the radiological guide 7 (see FIG. 8), each hole being disposed and oriented like the virtual guide cylinder on the two- and three-dimensional images. It is then possible to place a guide cylinder 9 in each hole, for example by means of a cylinder holder arranged on the positioning tool.

Figure 12:
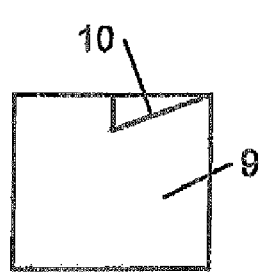
FIG. 12 depicts a view in side elevation of a guide cylinder according to the invention.

An embodiment of a guide cylinder of this type is shown in FIG. 12. This guide cylinder is provided with an external reference in the form of a recess 10 in its top edge. This recess has a sloping face, which preferably has an inclination in the direction of the turns of the future implant and a stop face parallel to the stop axis of the cylinder. The cylinders are placed so that this reference is visible from outside the mouth when the surgical guide is in place in the mouth of the patient. It must be understood that other types of reference can be imagined, for example one or more markings on the top edge of the cylinder. After placing, the cylinders 9 are fixed in their hole 8, for example by photopolymerisation of a suitable composite material. The surgical guide is now ready for use and receives the reference 11.

Production of the Definitive Prosthesis on the Pattern

Figure 16:
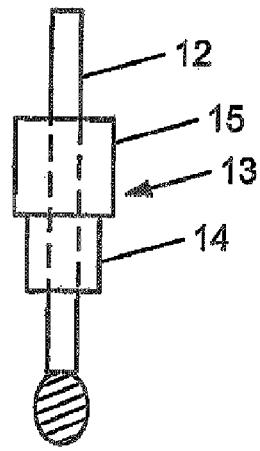
FIG. 16 depicts a drill bit to be used in a pattern.

This surgical guide 11 is placed on a pattern 1. Holes 16 are then drilled through the pattern, being guided by the cylinders 9 of the surgical guide (see FIG. 8). It is obviously possible, in order to avoid spoiling the cylinders 9 intended to guide the future surgical drilling in the mouth, to protect them by means of a protective cylinder (not shown), inserted inside the guide cylinders 9. It is possible to perform this drilling manually or by means of the positioning and drilling tool. One type of drill bit that can be used is illustrated, not to scale, in FIG. 16 by way of example. The shank of this drill bit 12 is passed through a drilling guide 13 in which it can slide and which comprises a bottom part 14 capable of sliding inside the guide cylinder 9 and a top part 15 having a diameter greater than the guide cylinder 9.

An implant analogue 17 having the type and dimensions of the implant selected when then two- and three-dimensional images are produced is then fixed to an analogue holder. Implant analogue means that it has the critical dimensions of the implant, namely its height and diameter in the top part. The implant analogue does not need to be provided with an external thread, nor to have a pointed shape like the majority of implants. In the example shown, it has a cylindrical shape provided on the surface with a retaining grove. It must on the other hand have a projecting head with a triangular, square or polygonal cross section identical to that of the future implant.

Figure 13:
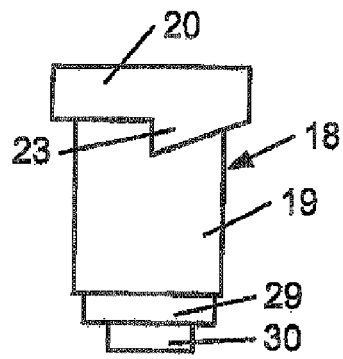
FIG. 13 depicts a view in side elevation of an analogue holder according to the invention.
Figure 14:
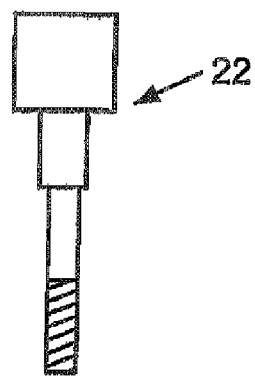
FIG. 14 depicts a screw for fixing the implant analogue to its analogue holder.
Figure 15:
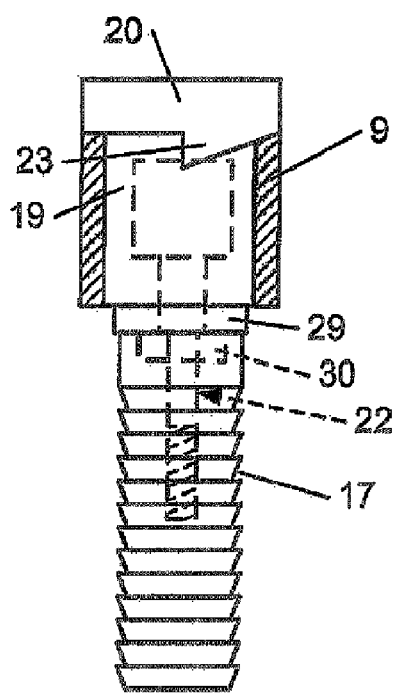
FIG. 15 depicts a view partially in section of the assembly of the implant analogue and its analogue holder.

An example of an analogue holder 18 is shown in isolation in FIG. 13. It has a cylindrical body 19 capable of sliding in the guide cylinder 9 as is illustrated in FIG. 15. It also comprises means of stopping the sliding in the form for example of an annual flange 20 with an outside diameter greater than the inside diameter of the guide cylinder 9. At its end opposite to the flange 20, the body 19 carries a washer 29 having a diameter less than that of the body but greater than or equal to that of the implant analogue, and a cylindrical projection 30 that can be gripped in a top cavity in the implant analogue 17. The thickness of the washer 29 will be chosen according to the appropriate distance to be provided between the guide cylinder and the implant analogue in position. A fixing screw 22, illustrated by way of example in FIG. 14, can be housed inside the analogue holder 18 in order to hold the implant analogue during the introduction thereof in the hole 16.

Figure 9:
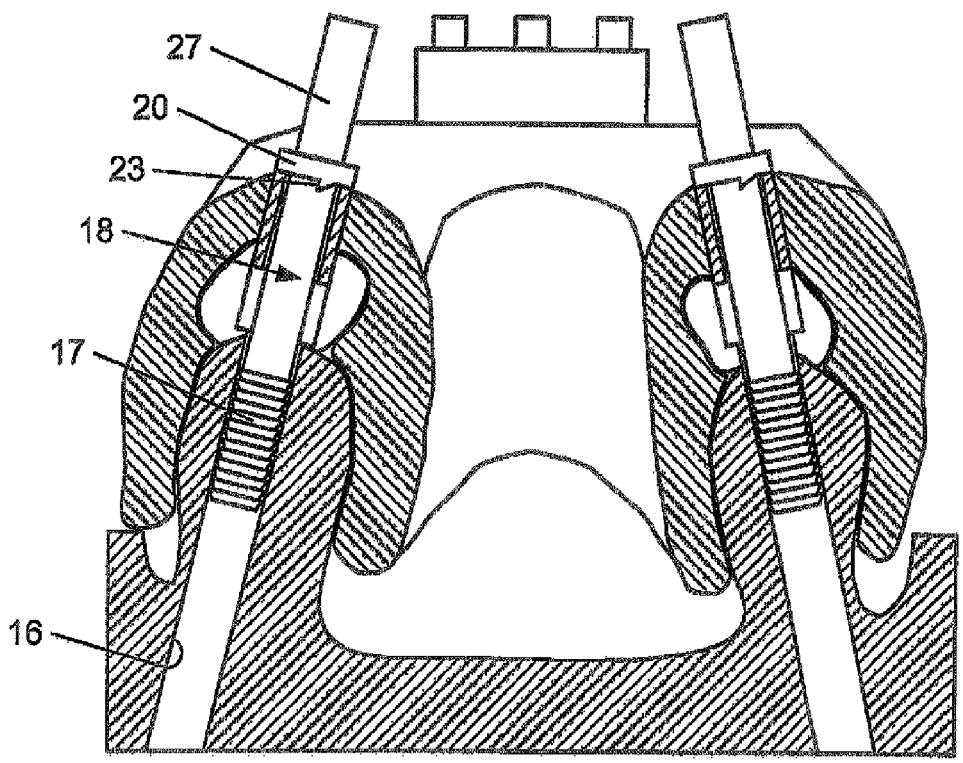
FIGS. 9 to 11 depict in the same view in section the steps of implanting implant analogues in the pattern and producing the definitive prosthesis on the implant analogues.

As can be seen on the analogue holder 18 shown schematically in FIG. 9, this can be provided with a sleeve 27.

The flange of the analogue holder 18 also carries at least one external reference, in the form for example of a downward projection 23 with a shape corresponding to that of the recess 10 in the top edge of the guide cylinder 9. In order to completely press the analogue holder 18 into the guide cylinder, it is therefore necessary to turn the analogue holder 18 about its axis until the projection 23 is locked in the recess 10. Therefore, when the analogue holder is introduced, the axially sliding thereof is stopped by contact between its flange 20 and the top edge of the guide cylinder 9, and the rotational position of the implant analogue is regulated by the abutment of the projection 23 on the face of the recess 10 that is parallel to the axis of the guide cylinder. This means that the implant analogue is in position, at the depth and in the orientation required according to the two- and three-dimensional images. The aforementioned head 24 of the implant analogue, which generally had a triangular to polygonal cross section, has thus received a given position in rotation with respect to the recess 10 in the guide cylinder.

Figure 10:
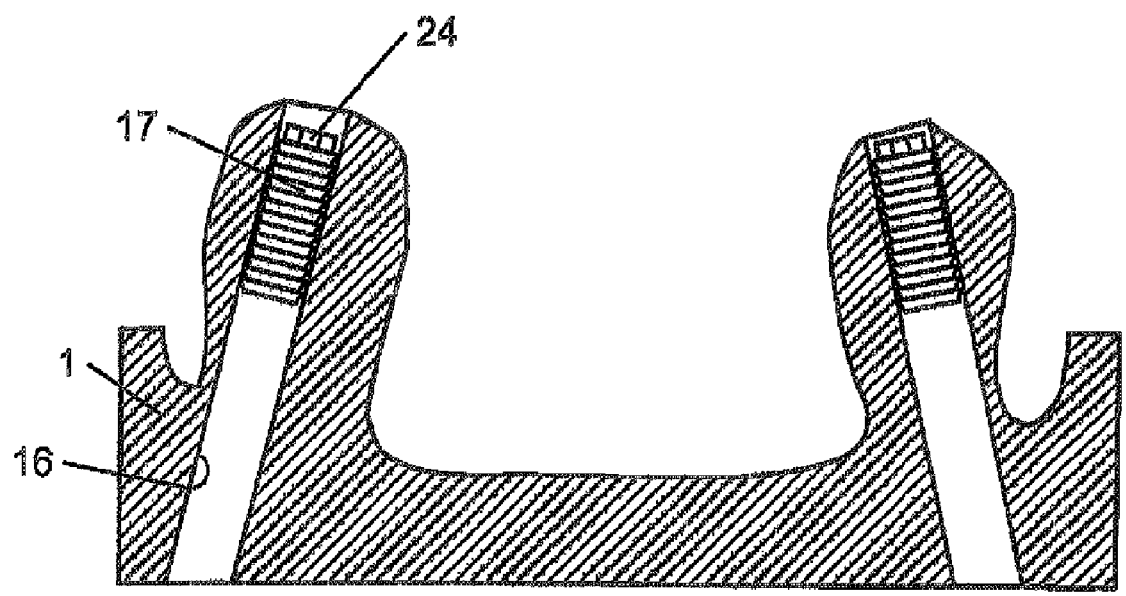
Figure 11:
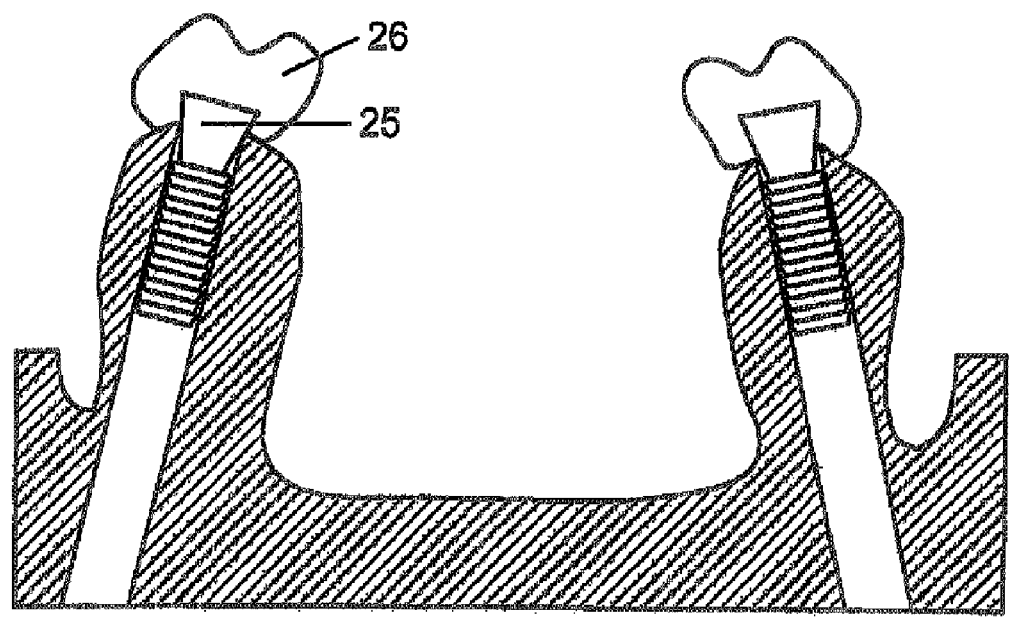

The position of the implant analogue 17 in the hole 16 is unique and perfectly determined. It is then fixed in the hole 16 for example by a suitable adhesive of the shrink-free polymerisable resin type that is introduced into the hole 16 through the back of the pattern 1. It is then possible to remove the analogue holder (see FIG. 10). The pattern is ready for producing the definitive prosthesis, for example bars, crowns or bridges, as is currently done after taking an impression of the jaw of the patient provided with implants, an impression produced several weeks after the fitting of the implants. A prosthesis in position on the pattern is illustrated in FIG. 11, where an abutment 25 has been fixed to each implant analogue with on top the corresponding definitive artificial tooth 26.

Fitting the Prosthesis

Next, the surgical guide 11 provided with its guide cylinders 9 is placed in the mouth of the patient.

Using surgical drill bits, holes are then drilled, through the guide cylinders, in the jaw in the same way as in the pattern. However, these drill bits, in addition to being guided in a correct orientation by the guide cylinders, are stopped in their sliding by a flange that they carry at a suitable height corresponding to the depth of the implant on the two- and three-dimensional images and which come to abut against the guide cylinder 9. Naturally this drilling can take place in stages, using different drill bits, in a normal and known manner.

Into each of these holes an implant is then introduced, similar to the implant analogue, by means of an implant holder similar to the analogue holder, that is to say provided with a means of stopping sliding, in the form for example of a flange, and a reference means, for example in the form of a downward projection capable of cooperating with the recess 10 in the guide cylinders 9. The implant is then pressed to the required depth in the appropriate orientation and its head, with a cross section identical to that of the implant analogue, has in rotation the same position as the head 24 of the implant analogue on which the prosthesis has been fashioned.

The position of the implants in the mouth is unique and corresponds perfectly to that of the implant analogues in the pattern, and to that appearing on the two- and three-dimensional radiological images. It is therefore possible to place there immediately the prosthesis that was fabricated before the implants were fitted.

One advantage to this technique is also that, by virtue of the anticipation of the prosthesis, the exact relative positions of the implants/prosthesis/bone are known and that all the safety features of depth, rotation and lateral positions are determined and fixed. Thus all human errors by drilling are excluded.

By virtue of this precision the possibility is obtained of creating implants (for example made from titanium or zirconium) in one piece (implants and stump) with a straight or angled stump, the final shape of which is terminated. The advantage of this type of implant is that it is no longer necessary to re-cut them in the mouth and because of this there is no propagation of heat through the implant to the bone during a homothetic reduction phase. And therefore the risk of rejection by burning of the bone is eliminated.

It must be understood that the present invention is in no way limited to the embodiment described above and that many modifications can be made thereto without departing from the scope of the present patent.

It is possible for example to make provision for modelling virtually bars, abutment elements, crowns or bridges from two- or three-dimensional images and to transmit these images and calculations to a machine tool that mills these prosthetic embodiments in metal blocks or ceramic materials. These images are produced on the basis of a colour contrast between the white created from the 30% by volume barium sulphate mixed with resin, which represents the prosthesis, and a variation in colour that represents the direct environment. These variations are expressed as a Hounsfield value. By virtue of this precise delimitation of the final result of the shape of the teeth, a 3D mesh can be created immediately. The editing of the edge and surface nodes can be modified by the computer operator by virtue of the orthographic views that he has available. After obtaining this morphological form on the basis of the image from the scanner, a homothetic reduction of the volume of the prosthetic element is carried out in order to have available a certain amount of space for placing the resin, the composite or the ceramic. These forms are then linked to the implants, the internal and external patterns of which are available as well as the form of the fixing screw. After finalisation of the virtual modellings the data are converted and exported in CAD format corresponding to the format required by the machine tool that is to mill the prosthetic base in a metal or ceramic block. After obtaining this prosthetic base, it is fixed to the analogues of the pattern, and the resin, composite or ceramic is applied in a conventional manner.

The invention claimed is:

1. Method of manufacturing a dental prosthesis to be implanted in a jaw of a patient, comprising the steps of:
producing, from an impression of the jaw of the patient, a radiological guide, provided with at least one artificial radiological tooth and radiological references,
processing, with a computer, radiological images in two dimensions representing the radiological guide in position on the jaw, so as to form, from the two-dimensional images, a three-dimensional image,
inserting per tooth, a virtual implant in a surgically appropriate position in the two- and three-dimensional images of the jaw
inserting, per tooth, a virtual guide cylinder oriented coaxially with the virtual implant in the two- and three-dimensional images of the radiological guide,
producing, from two- and three-dimensional data collected and calculated by the computer during the steps of image processing and of inserting the virtual implant and virtual guide cylinder, a surgical guide by first drilling, in each artificial tooth supported by the radiological guide, a first hole appropriate for receiving a guide cylinder disposed and oriented like the corresponding virtual guide cylinder of the images in two and three dimensions, and by placing in each first drilled hole such a guide cylinder provided with at least one external reference,
placing the surgical guide on a pattern obtained from the impression,
drilling, through each guide cylinder, a second hole through this pattern,
placing, in each second hole, an implant analogue by sliding into the guide cylinder an analogue holder that carries the implant analogue, as far as a depth corresponding to that of the virtual implant on the images in two and three dimensions, and by matching, by rotation, at least a second external reference provided on the analogue holder with the first external reference of the guide cylinder,
the implant analogue having dimensions corresponding to those of the virtual implant, selected for insertion in the images in two and three dimensions, which corresponds to a real implant to be placed in the jaw of the patient, and the implant analogue holder being identical to an implant holder selected for the implantation of the said real implant to be placed,
fixing the implant analogue in its hole, as placed, and
after removing each analogue holder and the surgical guide, making a definitive dental prosthesis adapted to the pattern provided with the implant analogue or analogues, this prosthesis thus being able to be fixed to the selected implants after they are implanted in the jaw in a manner that is guided by the surgical guide and identical to that used for the placing of the implant analogues in the pattern.

2. Method according to claim 1, further comprising:
fashioning, from the said impression, at least one pattern, on which there is produced a mounting provided with false teeth adaptable in the mouth,
producing a mounting key,
after removal of the said false teeth, pouring, in the key mounted on the pattern, a material visible in radiological imaging, and hardening it in the form of an arc,
dividing the hardened arc into individual artificial radiological teeth which, replaced in the key, are fixed on the pattern, and
after removing the key, producing the said radiological guide by depositing a self-hardening resin on the artificial radiological teeth fixed to the pattern.

3. Method according to claim 2, characterised in that the material visible in radiological imaging is a mixture of resin normal for fashioning artificial teeth and barium sulphate.

4. Method according to claim 1, characterised in that the manufacturing of the dental prosthesis further comprises a virtual modelling of prosthesis elements from the two- and three-dimensional images, a recording in the computer of data corresponding to the virtual images of these elements, transmission thereof to a machine tool, milling of these prosthesis elements by this machine tool in accordance with these data in a suitable manner and a fixing of these previously milled prosthesis elements to the implant analogues of the pattern.

5. Method according to claim 1, characterised in that the aforesaid processed radiological image is obtained by scanning.

6. Appliance intended for a dental prosthesis implantation in a jaw of a patient, comprising
at least one pattern (1) produced from an impression of the jaw of the patient, a radiological guide (7), also produced from this impression, and provided with at least one artificial radiological tooth (6) and radiological references (28), a computer, an image processing program for controlling the computer so as to make up, from a two-dimensional radiological image of the above-mentioned radiological guide in position on the jaw of the patient, a three-dimensional image and to insert, per tooth, a virtual implant selected in a surgically appropriate position in the two- and three-dimensional images of the jaw and a virtual selected guide cylinder orientated coaxially with the virtual implant in the two- and three-dimensional images of the radiological guide, a positioning and drilling tool in which the radiological guide (7) is positioned by means of its radiological references (28), this tool being capable, on the basis of data collected and calculated by the computer in relation to the images in two and three dimensions, to drill in each of the teeth of the radiological guide a first hole (8) in order to receive a guide cylinder (9) disposed and oriented like the virtual guide cylinder on the images in two and three dimensions, a guide cylinder (9) to be housed in each of the first holes (8) drilled in the radiological guide (7) that thus becomes a surgical guide (11), each guide cylinder being provided with at least one first external reference (10), a least a first drill bit (13) which, when the surgical guide (11) is in position on the pattern (1), can be guided through each guide cylinder (9) and is capable of drilling there, in the pattern, a second hole (16) according to the orientation of the corresponding guide cylinder, an implant analogue (17) corresponding to each virtual implant selected to be housed in each second drilled hole (16) in the pattern (1), using an analogue holder (18) to be slid axially through the corresponding guide cylinder (9), each analogue holder comprising stop means (20) that stop the sliding of the analogue holder (18) with respect to the guide cylinder (9) when the analogue (17) is in a position corresponding to the surgically appropriate position of the images in two and three dimensions, and at least one second external reference (23) to be matched, by rotation, with the said at least one first external reference (10) of the guide cylinder (9), a dental prosthesis (25, 26) adaptable to the pattern (1) provided with the above-mentioned implant analogue (17) or analogues, at least a second drill bit which, when the surgical guide (11) is in position on the jaw of the patient, can be guided through each guide cylinder (9) and is capable of drilling there third holes in the jaw according to the orientation of the guide cylinder, the said at least one second drill bit comprising stop means which, against the guide cylinder, stop a penetration of the drill bit at a depth that corresponds to that of the said surgically appropriate position of the virtual implant on the images in two and three dimensions, and an implant corresponding to each virtual implant selected to be housed in each third hole in the jaw by means of an implant holder to be slid axially through the corresponding guide cylinder, each implant and its implant carrier having dimensions and shapes identical to the implant analogue (17) and to its analogue holder (18) used in the pattern (1), each implant holder thus comprising stop means that stop the sliding of the implant holder in the guide cylinder (9) when the implant is in the above-mentioned surgically appropriate position, and at least a third external reference to be matched, by rotation, with the said at least one first external reference (10) of the guide cylinder (9), the implants thus fixed in the jaw being in position so as to receive the dental prosthesis (25, 26) previously implemented on the pattern (1).

7. The appliance according to claim 6, characterised in that each guide cylinder (9) on the one hand and each analogue holder (17) or each implant holder to be slid inside this guide cylinder on the other hand has mutual abutment means (10, 23) that stop a rotation movement of the analogue holder or implant holder with respect to the guide cylinder in a predetermined position, these stop means serving as aforementioned external first and second or respectively third references.

8. The appliance according to claim 6, characterised in that each guide cylinder (9) has an axial cavity having an inside diameter, each analogue holder (17) or implant holder or each second drill bit comprising a cylindrical part having an outside diameter allowing guided sliding of this part in the cavity of the guide cylinder (9) and a flange (20) having a diameter greater than said inside diameter, which serves as the aforementioned stop means.

9. The appliance according to claim 7, characterised in that each guide cylinder (9) has an axial cavity having an inside diameter, each analogue holder (17) or implant holder or each second drill bit comprising a cylindrical part having an outside diameter allowing guided sliding of this part in the cavity of the guide cylinder (9) and a flange (20) having a diameter greater than said inside diameter, which serves as the aforementioned stop means.

* * * * *